US008504388B2

(12) United States Patent
Seul et al.

(10) Patent No.: US 8,504,388 B2
(45) Date of Patent: Aug. 6, 2013

(54) METHOD AND APPARATUS FOR FULFILLING REQUESTS FOR PERISHABLE ITEMS

(75) Inventors: Michael Seul, Basking Ridge, NJ (US); Andreas E. Gocksch, Centerport, NY (US)

(73) Assignee: Bioinventors & Entrepeneurs Network, LLC, Warren, NJ (US)

( * ) Notice: Subject to any disclaimer, the term of this patent is extended or adjusted under 35 U.S.C. 154(b) by 0 days.

(21) Appl. No.: 13/366,702

(22) Filed: Feb. 6, 2012

(65) Prior Publication Data

US 2012/0203567 A1 Aug. 9, 2012

Related U.S. Application Data

(60) Provisional application No. 61/440,659, filed on Feb. 8, 2011.

(51) Int. Cl.
*G06Q 10/00* (2006.01)
*G06Q 50/00* (2006.01)
*G06Q 30/00* (2006.01)

(52) U.S. Cl.
USPC ............. 705/2; 705/3; 705/5; 705/6; 705/337

(58) Field of Classification Search
USPC ......................................... 705/2, 3, 5, 6, 337
See application file for complete search history.

(56) References Cited

U.S. PATENT DOCUMENTS

| 7,403,910 | B1 * | 7/2008 | Hastings et al. ............. 705/26.1 |
| 8,224,835 | B2 | 7/2012 | Kenedy et al. |
| 2002/0188495 | A1 * | 12/2002 | Banerjee et al. ................. 705/10 |
| 2005/0071245 | A1 * | 3/2005 | Norins et al. .................... 705/26 |
| 2005/0177435 | A1 * | 8/2005 | Lidow .............................. 705/22 |
| 2006/0205001 | A1 * | 9/2006 | Zhang et al. ....................... 435/6 |
| 2008/0010173 | A1 * | 1/2008 | Rendich et al. .................. 705/28 |
| 2008/0313059 | A1 * | 12/2008 | Martinek et al. ................ 705/28 |
| 2009/0150237 | A1 * | 6/2009 | Gupta et al. ..................... 705/14 |
| 2009/0204506 | A1 * | 8/2009 | Yoshida et al. ................. 705/26 |
| 2010/0250358 | A1 * | 9/2010 | Elkins et al. ............... 705/14.23 |
| 2011/0246274 | A1 * | 10/2011 | Mesaros .................... 705/14.19 |
| 2012/0109677 | A1 * | 5/2012 | Hillyer ............................. 705/2 |

OTHER PUBLICATIONS

Zettelmeyer et al., "Inventory Fluctuations and Price Discrimination: The Determinants of Price Varaiation in Car Retailing" Aug. 30, 2005 Econ 221 Industrial Organization Seminar UC Berkeley.*

Westcott et al., "The US Commodity Loan Program" Jan. 1, 2011.*

(Continued)

*Primary Examiner* — Neal Sereboff

(74) *Attorney, Agent, or Firm* — Drinker Biddle & Reath LLP

(57) ABSTRACT

Apparatuses, methods, and computer readable medium, for fulfilling a need for at least one perishable item, the method including reserving a plurality of perishable items with at least partially unknown attribute profiles from a supplier; receiving values for at least some of the reserved at least partially unknown attribute profiles, wherein the received values are determined by tests conducted after the reserving step; determining based on the received values which of the plurality of perishable items satisfy the need for the at least one perishable item; and if at least one of the plurality of perishable items does not satisfy the need for the at least one perishable item, unreserving the at least one perishable item of the plurality of perishable items determined not to satisfy the need for the at least one perishable item.

21 Claims, 11 Drawing Sheets

OTHER PUBLICATIONS

Powerscource Press LLC, "Bringing a New Car From Another Dealership—Dealership Trades" web page from Dec. 9, 2010.*

Manning et al., editors "Blood Donors and the Supply of Blood and Blood Products" Form on Blood Safety and Blood Availability, Institute of Medicine 1996.*

Definition—attribute—from Google dictionary as downloaded on Oct. 16, 2012.*

Anonomous, "Inventory Carrying Costs: Is there a Right Way to caclulate them?" Inventory Reduction Report, Aug. 2001 Issue Aug. 2001.*

Definition—Cost of Goods Sold—from Investopedia, as downloaded on Oct. 16, 2012.*

* cited by examiner

| Blood Group System | Antigens |
|---|---|
| ABO | A, B, H |
| Rh | E, e |
| Kell | K, k |
| Scianna | Sci, Scii |
| Dombrock | Do$^a$, Do$^b$, Hy, Jo |

| Blood Group System | Antigen | Present? |
|---|---|---|
| ABO | A | 1 |
|  | B | 0 |
|  | H | 0 |
| RhE | E | 1 |
|  | e | 0 |
| Kell | K | X |
|  | k | X |
| Scianna | Sci | 1 |
|  | Scii | 0 |
| Dombrock | Do$^a$ | 1 |
|  | Do$^b$ | 0 |
|  | Hy | X |
|  | Jo | X |

| Blood Group System | Antigen | Present? |
|---|---|---|
| ABO | A | 1 |
|  | B | 0 |
|  | H | 0 |
| RhE | E | 1 |
|  | e | 0 |
| Kell | K | X |
|  | k | X |
| Scianna | Sci | 0 |
|  | Scii | 1 |
| Dombrock | Do$^a$ | 1 |
|  | Do$^b$ | 0 |
|  | Hy | X |
|  | Jo | X |

| Blood Group System | Antigen | Present? |
|---|---|---|
| ABO | A | 1 |
|  | B | 0 |
|  | H | 0 |
| RhE | E | 1 |
|  | e | 0 |
| Kell | K | 0 |
|  | k | 0 |
| Scianna | Sci | 0 |
|  | Scii | 0 |
| Dombrock | Do$^a$ | 1 |
|  | Do$^b$ | 0 |
|  | Hy | X |
|  | Jo | X |

FIG. 2D

METHOD AND APPARATUS FOR FULFILLING REQUESTS FOR PERISHABLE ITEMS

CROSS REFERENCE TO RELATED APPLICATION

This application claims the filing date benefit of U.S. Provisional Application No. 61/440,659, filed Feb. 8, 2011, the entire disclosure of which is incorporated herein by reference.

FIELD

The present disclosure relates to methods and apparatuses for fulfilling requests for perishable inventory and more particularly to methods and apparatuses for fulfilling requests for perishable inventory where the perishable inventory has some unknown attributes that need to be determined to fulfill the request.

BACKGROUND

In the discussion of the background that follows, reference is made to certain structures and methods. However, the following references should not be construed as an admission that these structures and methods constitute prior art. Applicants expressly reserve the right to demonstrate that such structures and methods do not qualify as prior art.

Replacement human blood is vital to medical treatment. Many medical treatments including many operations would not be possible without blood being available to replace blood lost during medical procedures and injuries. Blood, contains cellular components, principally red blood cells ("erythrocytes"), platelets ("thrombocytes") and white blood cells ("leukocytes"), suspended in plasma.

One problem in supplying replacement blood is that it is perishable. As soon as blood is collected, red cells within the blood may acquire "storage lesions," which may reduce the effectiveness of these cells to deliver oxygen to tissue. Moreover, freezing and thawing may damage cells and reduce their effectiveness. The blood may also acquire inflammatory factors especially when white cells are allowed to remain. The blood may also contain infectious agents that may proliferate, especially when blood components are stored at room temperature as is the case for platelets. For these reasons, fresh blood is more effective and, in practice is preferred over older blood. Regulatory agencies have set the time period for using red blood cells to forty-two (42) days after collection, and have set the time period for using platelets to only five (5) days (or seven days provided special storage conditions are ensured) due to the risk of proliferation of bacteria as platelets are stored at room temperature. Expired blood components are no longer suitable for human use. In the United States of America, approximately 400 thousand of 1.675 million units of red blood cells collected, and approximately 200 thousand of 1.810 million units of (single donor) platelets collected expire before use.

Another problem in supplying replacement blood is that the replacement blood is typically matched to the recipient's blood type only with respect to an abbreviated blood type such as A+, AB−, or O−, which indicates the presence ("A", "B" or "AB") or absence ("O") of the antigens within the ABO blood group system and "+" or "−", which indicates the presence or absence (by traditional "agglutination" testing) of the D antigen, a constituent of the RH blood group system. However, the International Society of Blood Transfusion to date has defined thirty (30) blood group systems each of which may include multiple antigens.

The set of antigens expressed on an individual's blood cells is referred to herein as an attribute profile or an antigen profile. Any of the antigens associated with molecules on cell surfaces of replacement blood cells may cause the recipient's immune system to treat the replacement blood as foreign if the recipient's own blood cells do not have the same antigens as the replacement blood antigens. This may lead to immune reactions and adverse clinical events. Adverse immune reactions may be mild and have no significant effect on the recipient or may be severe and life threatening. Seventy-two thousand (72,000) adverse transfusion-related events were reported in 2006. Determining the identity of individual antigens, or the identity of an entire set of antigens of a replacement blood unit may be prohibitively time consuming and expensive. Often, in the United States of America, routine antigen testing prior to red blood cell transfusion is limited to the principal antigens, A, B and D, and typically is omitted altogether prior to platelet transfusion.

Another problem in supplying replacement blood is the way in which blood is collected and distributed. Blood units are often collected from donors residing in a given local area, and are distributed to local hospitals that perform the surgical or other procedures requiring transfusion support. The cost of a blood unit may vary significantly by geographic area for many reasons including labor costs and the availability of donors. As blood units often are only distributed locally or regionally shortages may occur in some locations while surpluses occur in other locations. Additionally, it may be prohibitively time consuming or expensive for a health care provider to locate and procure a blood unit with particular attributes.

These same problems are often common problems for perishable items with attributes that may require testing to determine the attribute profile of the perishable items prior to use.

SUMMARY

Therefore, there is a need in the art for a method of fulfilling a need for at least one perishable item. The method including reserving a plurality of perishable items with at least partially unknown attribute profiles from a supplier; receiving values for at least some of the reserved at least partially unknown attribute profiles, wherein the received values are determined by tests conducted after the reserving step; determining based on the received values which of the plurality of perishable items satisfy the need for the at least one perishable item; and if at least one of the plurality of perishable items does not satisfy the need for the at least one perishable item, unreserving the at least one perishable item of the plurality of perishable items determined not to satisfy the need for the at least one perishable item. The method may include transforming the reserved plurality of perishable items with at least partially unknown attribute profiles into a plurality of perishable items with at least partially known attribute profiles using the received values.

The method may include if at least one of the plurality of perishable items does satisfy the need for the at least one perishable item, fulfilling the need for the at least one perishable item with the at least one of the perishable items determined to satisfy the need.

The perishable item may be a blood unit.

The attribute profiles may be antigen profiles.

Determining may include determining based on the received values which of the plurality of perishable items satisfy the need for the at least one perishable item by comparing attribute profiles of the reserved plurality of perishable items with attribute profiles of each of the needed at least one perishable item.

A perishable item of the reserved at least on plurality of perishable items may satisfy the need for the at least one perishable item if the attribute profile of the perishable item of the reserved at least one perishable does not indicate a presence of an antigen when the needed at least one perishable item indicates an absence of the corresponding antigen.

The method may include determining a number of the plurality of perishable items to reserve based at least on the needed at least one perishable item.

The method wherein the step of reserving may include receiving title to the plurality of perishable items with at least partially unknown attribute profiles from the supplier in exchange for a loan; and the step of unreserving may include if at least one of the plurality of perishable items does not satisfy the need for the at least one perishable item, transferring the title to the at least one perishable item that does not satisfy the need back to the supplier in exchange for repayment of the loan, and if at least one of the plurality of perishable items does satisfy the need for the at least one perishable, replenishing the supplier with at least one equivalent perishable item for the at least one of the plurality of perishable items that does satisfy the need.

The loan may be below a market rate for loans.

The plurality of perishable items with at least partially unknown attributes may be collateral for the loan.

The method wherein the step of reserving includes reserving a plurality of perishable items with at least partially unknown attribute profiles from a supplier for a limited time period, the limited time period being less than a time period in which the plurality of perishable items will perish; and wherein the step that begins if at least one may include if at least one of the plurality of perishable items does not satisfy the need for the at least one perishable item, unreserving at least one perishable item of the plurality of perishable items determined not to satisfy the need for the at least one perishable item before the limited time period has elapsed.

The step of reserving may include reserving a plurality of perishable items with at least partially unknown attribute profiles from a supplier for a limited time period, the limited time period being less than a time period required to receive values for at least some of the at least partially unknown attribute profiles.

The step of reserving may include entering into a conditional sale agreement for a plurality of perishable items with at least partially unknown attribute profiles from a supplier; and wherein the step that begins if at least one of the plurality of perishable items may include if at least one of the plurality of perishable items does not satisfy the need for the at least one perishable item, not exercising the conditional sale agreement for at least one perishable item of the plurality of perishable items determined not to satisfy the need for the at least one perishable item, and if at least one of the plurality of perishable items does satisfy the need for the at least one perishable item, exercising the conditional sale agreement for at least one perishable item of the plurality of perishable items determined to satisfy the need for the at least one perishable item.

The step of receiving values for at least some of the at least partially unknown attribute profiles may include instructing the supplier to send a part of each of the plurality of perishable items with at least partially unknown attribute profiles to a laboratory for testing; and receiving results of the testing as values for at least some of the at least partially unknown attribute profiles.

The method may include instructing the laboratory how to perform the testing.

The method may include sharing the results of the testing with the supplier in at least partial exchange for the supplier reserving the plurality of perishable items with at least partially unknown attribute profiles.

The perishable item may be a blood unit, and the part of each of the plurality of perishable items may be a blood aliquot.

The method may include paying the supplier a fee to send a part of each of the plurality of perishable units with at least partially unknown attribute profiles to a laboratory for testing.

The method may include if at least one of the plurality of perishable items does satisfy the need for the at least one perishable item, replenishing the supplier with an equivalent perishable item for the at least one of the plurality of perishable items that does satisfy the need for the at least one perishable item.

The step of reserving may include reserving a plurality of perishable items with at least partially unknown attribute profiles from a supplier for a limited amount of time in exchange for performing a partial attribute check, the partial attribute check being necessary prior to the plurality of perishable items being used.

At least some of the steps of the method may be executed by a processor of a computer.

The step of determining may include sending the received values to a perishable item requester; and determining based on the received values which of the plurality of perishable items satisfy the need for the at least one perishable item by receiving a determination of which of the plurality of perishable items satisfy the need from the perishable item requester.

A method of fulfilling a need for a blood unit is disclosed. The method may include entering into a conditional sale agreement for a plurality of blood units with at least partially unknown attribute profiles from a supplier; receiving values for at least some of the at least partially unknown attribute profiles; determining based on the received values which of the plurality of blood units satisfy the need for the blood unit; if at least one of the plurality of blood units does not satisfy the need for the blood unit, not exercising the conditional sale agreement for the at least one of the plurality of blood units determined not to satisfy the need for the at least one blood unit; if at least one of the plurality of blood units does satisfy the need for the blood unit, exercising the conditional sale agreement for the at least one of the plurality of blood units determined to satisfy the need for the at least one blood unit; and fulfilling the need for the blood unit with the at least one of the plurality of blood units determined to satisfy the need for the at least one blood unit, wherein at least one step is executed by a processor of a computer.

The step of receiving values for at least some of the at least partially unknown attribute profiles may include instructing the supplier to send a part of each of the plurality of blood units with at least partially unknown antigen profiles to a laboratory for testing; representing the plurality of blood units with at least partially unknown antigen profiles in a computer memory; receiving values for at least some of the at least partially unknown antigen profile; and updating the representation of the plurality of blood units with at least partially unknown antigen profiles with the received values.

The method may include determining, by use of the processor, a number of the plurality of perishable items based on a probability of finding an antigen profile that will satisfy the need for the blood unit.

A computer program product is disclosed. The computer program produce may include a first set of codes for reserving a plurality of perishable items with at least partially unknown attribute profiles from a supplier; a second set of codes for receiving values for at least some of the at least partially unknown attribute profiles; a third set of codes for determining based on the received values which of the plurality of perishable items satisfy a need for the at least one perishable item; and a fourth set of code for unreserving at least one perishable item of the plurality of perishable items determined not to satisfy the need for the at least one perishable item, if at least one of the plurality of perishable items does not satisfy the need for the at least one perishable item.

A computer system for fulfilling a need for at least one perishable item is disclosed. The computer system may include a process adapted to: reserve a plurality of perishable items with at least partially unknown attribute profiles from a supplier; receive values for at least some of the at least partially unknown attribute profiles; determine based on the received values which of the plurality of perishable items satisfy the need for the at least one perishable item; and unreserve at least one perishable item of the plurality of perishable items determined not to satisfy the need for the at least one perishable item, if at least one of the plurality of perishable items does not satisfy the need for the at least one perishable item.

It is to be understood that both the foregoing general description and the following detailed description are exemplary and explanatory and are intended to provide further explanation of the invention as claimed.

BRIEF DESCRIPTION OF THE DRAWINGS

The following detailed description can be read in connection with the accompanying drawings in which like numerals designate like elements and in which:

FIG. 2A illustrates some of the known red blood cell antigens.

FIGS. 2B, 2C, and 2D illustrate an antigen profile for red blood cells of a blood unit.

DETAILED DESCRIPTION

Figure 1:
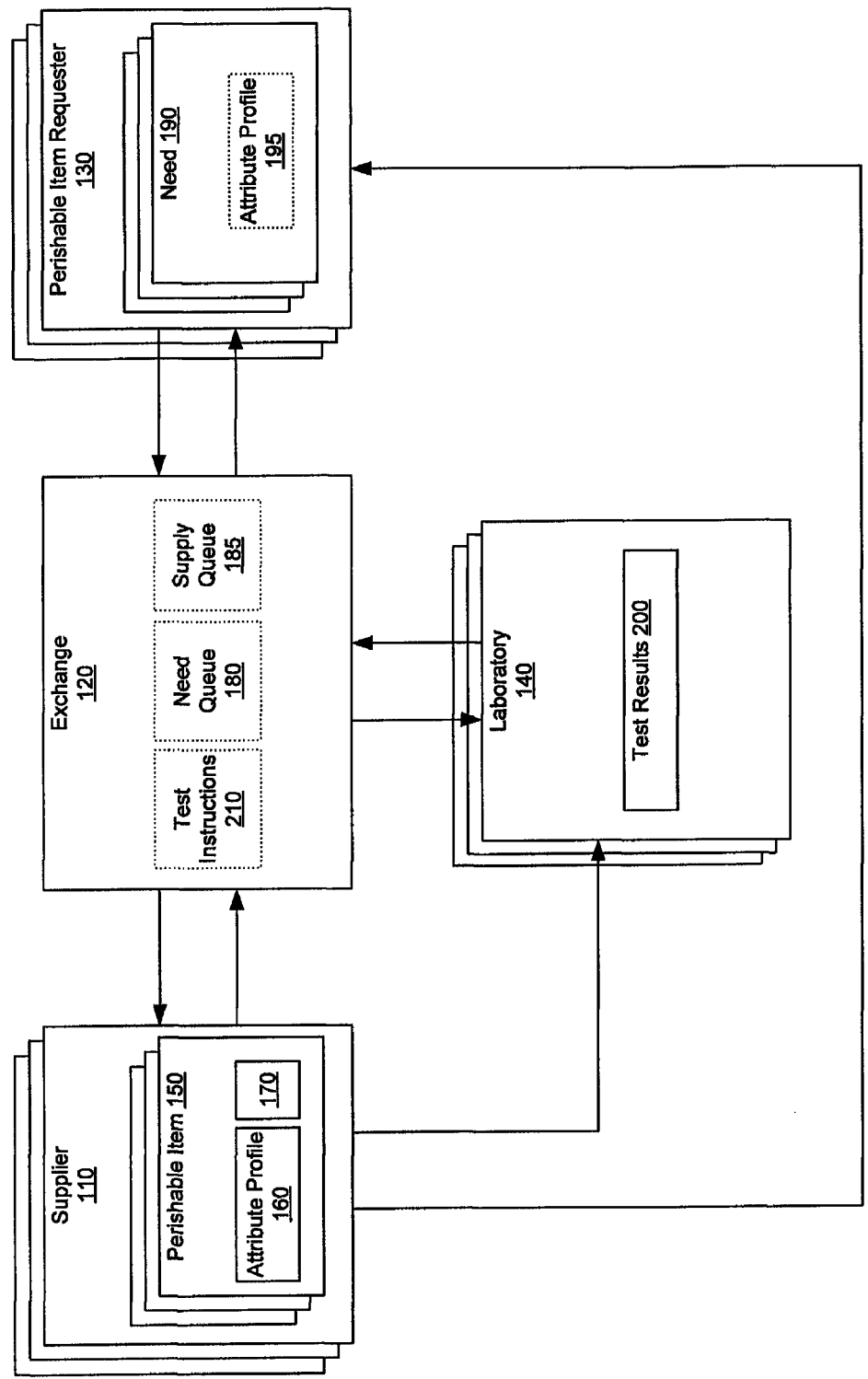
FIG. 1 is an illustration of an embodiment of a system for fulfilling a need for perishable items.

FIG. 1 is an illustration of an embodiment of a system for fulfilling a need for perishable items. Illustrated in FIG. 1 are a supplier 110, an exchange 120, a perishable item requester 130, and a laboratory 140. There may be multiple suppliers 110, multiple perishable item requesters 130, and multiple laboratories 140. The exchange 120 attempts to fulfill a need 190 for one or more perishable items 150 by reserving one or more perishable items 150 from the supplier 110. The exchange 120 then receives values for some of the attributes of the attribute profiles 160 of the reserved perishable items 150. The exchange 120 may then unreserve perishable items 150 determined not to satisfy the need for the perishable items 150. The exchange 120 may fulfill the need for the perishable items 150 with perishable items 150 determined to satisfy the need for the perishable items 150. The need for the one or more perishable items 150 may come from the perishable item requester 130 as a request 190 or the exchange 120 may determine that the supply queue 185 needs perishable items 150.

The perishable item requester 130 sends a need 190 to the exchange 120 for perishable items 150 that have an attribute profile 160 compatible with attribute profile 195. The perishable item requester 130 may be a hospital, a doctor's office, a health insurance carrier or an entity that requests perishable items 150. The perishable items 150 may be blood units 150. The attribute profiles 160, 195 may include multiple attributes and each attribute may be either known or unknown. If the attribute is known, then the attribute may have a value indicating an attribute of the perishable item 150. For example, if the perishable item 150 is a blood unit 150, then the attribute profile 160, 195 may be an antigen profile 160. The antigen profile 160 may be a profile of thirty-two (32) different red blood cell antigens. The antigen profile 160 may then have thirty-two (32) values one for each of the thirty-two antigens. Each value of the antigen profile 160 may be a "1" indicating the presence of the corresponding antigen, a "0" indicating the absence of the corresponding antigen, or "X" indicating that it is unknown whether or not the red blood cell has the corresponding antigen. Antigen profiles are discussed more below. The need 190 may indicate that the exchange 120 is to find a perishable item 150 with an attribute profile 160 compatible with the attribute profile 195. The attribute profile 195 and/or the need 190 that the perishable item requester 130 sends the exchange 120 may include rules or other indications of how the exchange 120 may determine whether or not an attribute profile 160 of a perishable item 150 satisfies the need 190. The need 190 may indicate that the attribute profile 195 is to be matched with the attribute profile 160 of a perishable item 150. For example the attribute profile 195 may have "1" to indicate that an attribute of the needed perishable item 150 should be present, a "0" to indicate an attribute should not be present, or an "X" to indicate that the attribute may or may not be present. The perishable item requester 130 may send a need 190 without an attribute profile 195. The perishable item requester 130 may send test instructions 210 with the need 190. Moreover, the exchange 120 and/or the supplier 110 and/or the laboratory 140 may send the perishable item requester 130 test results 200 and the perishable item requester 130 may then determine which of the perishable items 150 reserved by the exchange 120 satisfy the need 190 of the perishable item requester 130.

The supplier 110 supplies perishable items 150 with attribute profiles 160. The supplier 110 may be a blood bank, a hospital, or an entity that supplies perishable items 150. The supplier 110 may take a sample 170 of the perishable item 150 and send the sample 170 to the laboratory 140 for testing. The supplier 110 may receive from, or send to, the exchange 120: instructions for sending samples 170, title to the perishable items 150, test results 200, reservations for perishable items 150, unreservations for perishable items 150, fees, and/or compensation. The supplier 110 may send perishable items 150 to the perishable item requester 130. The supplier 110 may combine in one shipment multiple samples 170 before sending the samples 170 to the laboratory 140.

The laboratory 140 takes a sample 170 of a perishable item 150 and performs tests according to test instructions 210 to produce test results 200. The laboratory 140 may be a laboratory that is certified to be in compliance with applicable regulations of the Clinical Laboratory Improvement Act ("CLIA") and may be a commercial laboratory, or non-profit laboratory. The laboratory 140 may be a legally independent entity or a subsidiary of another entity. The laboratory 140 may be physically part of the exchange 120, the supplier 110 and/or the perishable item requester 130. The laboratory 140 may receive test instructions 210 from the exchange 120 and/or from the supplier 110. The laboratory 140 may receive one or more samples 170 for testing, and may combine samples 170 for testing. The test results 200 may be used to determine the value of unknown attributes of the attribute profile 160 so that the attribute is a known attribute (rather than an unknown attribute) of the attribute profile 160. For example, continuing with the blood example above, the laboratory 140 may take an aliquot 170 (which is a sample of blood from a blood unit 150) sent from the supplier 170 and perform tests on the aliquot 170 to determine the one or more antigens. The test results 200 will indicate the presence or absence of the antigens for the aliquot 170 within the attribute profile 160 of the blood unit 150. The test results 200 may need interpretation and the laboratory 140 may send the test results 200 to the exchange 120 and/or the perishable item requester 130. The exchange 120 may use the test results 200 to transform an unknown attribute of an attribute profile 160 into a known attribute of an attribute profile 160.

The exchange 120 receives needs 190 for perishable items 150 with attribute profiles 195 from the perishable item requester 130 and fulfills the needs 190 with perishable items 150 from the supplier 110 that are determined to satisfy the need 190. The exchange 120 may be implemented on a computer and the exchange may communicate with the perishable item requester 130, the supplier 110, and/or the laboratory 140 via communication networks. The exchange 120 may include one or more of the following: test instructions 210, a need queue 180, and a supply queue 185. The test instructions 210 may be instructions for the laboratory 140 to perform tests on the samples 170 of the perishable items 150. The need queue 180 may be a queue where needs 190 are placed. The supply queue 185 may be a supply of perishable items 150 that the exchange 120 maintains. For example, the supply queue 185 may maintain a supply of perishable items 150 that are perishable items 150 from suppliers 110 that the exchange 120 either has reserved or may know that the supplier 110 has the perishable item 150 available. There may be an inventory system that shares inventory information between the supplier 110 and the exchange 120. The exchange 120 may receive a need 190 from a perishable item requester 130. The exchange 120 may place the need 190, or may permit the perishable item requester 130 to place the need 190, into a need queue 180 of needs 190. The exchange 120 may generate a need 190 based on needing additional perishable items 150 for the supply queue 185. The exchange 120 may receive from, or send to the supplier 120 test instructions 210, title to the perishable items, test results 200, reservations, unreservations, and/or compensation. The exchange 120 may reserve perishable items 150 by arrangement with the supplier 110. The exchange 120 may determine which of a number of perishable items 150 to reserve with the supplier 110 based on one or more attribute profiles 195 in the need queue 180. The exchange 120 may send to the supplier 110 instructions to send samples 170 to the laboratory 140. The exchange 120 may send test instructions 210 to the laboratory 140 for the laboratory 140 to follow to perform tests on samples 170 and to report the test results 200. The test instructions 210 may be based on one or more requests 190 in the request queue 180 and on a number of samples 170. The exchange 120 may receive test results 200 from the laboratory and/or the supplier 110 and take the test results 200 and transform at least one attribute of an attribute profile 160 from being unknown to being known. As is discussed in more detail below, the exchange 120 may reserve the perishable items 150 by way of a conditional sales agreement, a repurchase agreement, fees and/or another form of compensation. The exchange 120 may unreserve perishable items 150 by not exercising its right to acquire these items, closing repossession agreements, closing repurchasing agreements, exchanging or reversing fees, and/or another form of compensation. The exchange 120 may determine whether or not a perishable item 150 satisfies a need 190 based on one or more of the following: the attribute profile 160, the attribute profile 195, the need 190, the test results 200, the test instructions 210, the need queue 180 and/or which perishable items 150 are in the supply queue 185.

In operation, the exchange 120 receives a need 190 for a perishable item 150. The need 190 may include an attribute profile 195. For example, the exchange 120 may receive a need 190 for a blood unit 150 with an antigen profile 160 that includes a value of "0" or not present for the antigen "e". For this example, to satisfy the need 190, the exchange 120 may need to find a blood unit 150 that has an antigen profile 160 with a value "0" or not present for the antigen "e" for the blood unit 150.

Alternatively, the need 190 may indicate that the exchange 120 is to find a perishable item 150 with an attribute profile 160 compatible with an attribute profile 195 sent to the exchange 120. For example, the need 190 may include an attribute profile 195 of a patient with a value of "0" for the antigen "e". The exchange 120 may then use compatibility rules to determine that for an attribute profile 160 to be compatible with the attribute profile 195 that the attribute profile 160 must have a value of "0" for the antigen "e".

Alternatively, or in addition, the need 190 may include rules for the exchange 120 to use to determine whether or not an attribute profile 160 satisfies the need 190.

To attempt to satisfy the need 190, the exchange 120 reserves a number of perishable items 150 from a supplier 110. The exchange 120 may determine the number of perishable items 150 to reserve based on calculating how many perishable items 150 may be needed to find a perishable item 150 that is compatible with the attribute profile 195 of the request 190. In embodiments, the exchange 120 may determine the number based on multiple needs 190 in the need queue 180, based on expected needs 190, and/or based on supply in the supply queue 185. In embodiments, the need 190 may include an indication of the number of perishable items 150 to reserve. Additionally, note that in the example above that only a single antigen was considered but the antigen profile 195 may contain many more antigens that may need to be considered when determining whether or not the antigen profile 160 of the blood unit 150 will satisfy the need 190.

The exchange 120 receives values for the attribute profiles 160 of the reserved perishable items 150. For example, the exchange 120 may instruct the supplier 110 to send a sample 170 of each of the number of reserved perishable items 150 to the laboratory 140 for testing. The exchange 120 may then send test instructions 210 to the laboratory 140 which instruct the laboratory 140 how to perform tests on the samples 170. The exchange 120 may then receive the test results 200 from the laboratory 140. The exchange 120 may then use the test results 200 to determine whether the reserved perishable items 150 satisfy the need 190.

For example, continuing the example above, suppose the exchange 120 had reserved one-hundred (100) blood units 150 from the supplier 110 to find a blood unit 150 satisfying the need 190 with the antigen profile 195. Aliquots (blood samples) 170 from the one-hundred (100) blood units 150 would be sent to the laboratory 140 for testing according to the test instructions 210. The laboratory 140 would generate test results 200 and may send the test results 200 to the exchange 120. The exchange 120 would use the test results 200 to determine which (if any) of the one-hundred (100) blood units 150 satisfies the need 190. In embodiments, the exchange 120 or the laboratory 140 may send the test results 200 to the perishable item requester 130 which may then determine which (if any) of the reserved perishable items 150 satisfy the need 190. The perishable item requester 130 may then send an indication of which of the reserved perishable items 150 for the exchange 150 to unreserve.

The exchange 120 may then unreserve from the supplier 110 the perishable items 150 that are not needed to satisfy the need 190. Continuing the example above, the exchange 120 may unreserve ninety-nine (99) blood units 150 that had a value of "1" (present) in the antigen profile for antigen "e" and not unreserved one (1) blood unit 150 that has a value of "0" (not present) in the antigen profile for antigen "e".

As another example, the exchange 120 may generate a need 190 for additional perishable items 150 for the supply queue 185. The need 190 may only indicate a number of perishable units 150 to reserve and may indicate test instructions 210 for the laboratory 140 to use as well as conditions for reserving and unreserving the perishable units. The exchange 120 may then reserve the number indicated in the need 190 of perishable units 150 from the supplier 110. The exchange 120 may reserve the perishable units 150 according to conditions specified in the need 190 or according to conditions not specific in the need 190. Samples 170 from the supplier 110 would be sent to the laboratory 140 for testing according to the test instructions 210, which may be included with the need 190. The test results 200 may then be sent to the exchange 120. The exchange 120 may then determine whether or not the reserved perishable items 150 satisfy the need 190 based on the test results 200. The supply queue 185 may maintain one or more perishable items 150 to satisfy needs 130 from perishable item requester 130. To determine which of the reserved perishable items 150 satisfy the need 190 may include checking bins in the supply queue 185 and to see if a reserved perishable item 150 will fit into a bin that may need additional perishable items 150. In embodiments, the supply queue 185 may be in a separate module and the exchange 120 may send the test results 200 to the separate module which may determine which if any of the reserved perishable items 150 satisfy the need 190.

In embodiments, the exchange 120 may use the test results 200 to transform the unknown attributes of attribute profiles 160 into known attributes of the attribute profile 160. In embodiments, the exchange 120 may reserve new blood units 150 if the need 190 is not satisfied.

The exchange 120 may fulfill the need 190 with the perishable item 150 that satisfies the need 190. Continuing the example above, the exchange 120 may instruct the supplier 110 to ship the blood unit 150 with the antigen profile of "0" (not present) for antigen "e" to the perishable item requester 130. In embodiments, the exchange 120 may instruct the perishable item requester 130 to instruct the supplier 110 to ship the blood unit 150 with the antigen profile of "0" (not present) for antigen "e" to the perishable item requester 130. The steps described above may be carried out in a different order.

A problem the exchange 120 may have is how to reserve the perishable units 150 such that they are held for an agreed upon period by the supplier 110, for possible acquisition by the exchange 120 and/or the perishable item requester 130. The exchange 120 may reserve a number of perishable units 150, under an arrangement with the supplier 110, to find a perishable unit 150 with the attribute profile 195 that satisfies the need 190. Under such an agreement, the supplier 110 will agree to not sell the reserved perishable units 150 until the exchange 120 determines which of the perishable items 150 with the attribute profile 195 satisfy the need 190. One way the exchange 120 may reserve the perishable items 150 is to purchase the perishable items 150, but it may not be economically feasible to purchase the perishable items 150 from the supplier 110 as the exchange 120 may need to reserve many perishable items 150 in order to find a perishable item 150 compatible with the attribute profile 195 of the request 190. Additionally, the exchange 120 may not be able sell the perishable items 150 that are not compatible with the attribute profile 195 of the request. When the perishable item 150 is blood units 150 there are no derivatives and no means of "shorting" a blood unit 150, which are financial instruments that are available with some perishable items 150 such as corn.

A problem the supplier 110 may have is that the supplier 110 may not have a predictable supply of perishable items 150. For example, with blood units 150, the number of people that may donate on any given day may depend on many factors that are not under the control of the supplier 110. For example, it may rain one day which may make people less likely to participate in a blood collection scheduled on that day. Additionally, the supplier 110 may incur a delay in replenishing inventory following blood collection, as a time period may be required to complete mandatory testing of the perishable items 150 prior to their being eligible for sale. The supplier 110 thus may find itself with a limited supply of perishable items 150 so that if the exchange 120 happens to find many perishable items 150 that are compatible with pending requests 190, the supplier 110 may not be able to supply both the exchange 120 and other perishable item requesters 130.

FIG. 2A illustrates some of the known red blood cell antigens. Antigens in red blood cells are grouped by thirty (30) known blood group systems. Over six-hundred (600) antigens in red blood cells have been discovered so far. Five blood group systems of the thirty known blood group systems are illustrated in FIG. 2A. The blood group systems illustrated are ABO, Rh, Kell, Scianna, and Dombrock, which have respectively antigens A, B; E, e; K, k; Sci, Scii; and $Do^a$, $Do^b$, Hy, Jo. Some of the blood group systems include additional antigens that are not illustrated. For example, the Rh blood group system has fifty (50) defined blood-group antigens among including the antigens D, C, c, E, and e with only "E" and "e" illustrated in FIG. 2A.

Many of the names of the blood group systems are taken from the names of patients that were first discovered to have a reaction to an antigen.

FIGS. 2B, 2C, and 2D illustrate an antigen profile for red blood cells of a blood unit. As discussed above, the antigen profiles may have three values "1", "0", and "X". "1" indicates the antigen has been determined to be present on the red blood cells. "0" indicates that the antigen has been determined to not be present on the red blood cells. "X" indicates that it has not been determined whether or not the antigen is present on the red blood cells. The attribute profile may be represented in different ways to convey the same information. The attribute profile may be an indication of a desired antigen profile to fill the need 190. The International Society of Blood Transfusion (ISBT) has a system for naming an antigen of a red blood cell that is different from the system described here.

The attribute profile 195 of FIG. 2B is "10010XX1010XX". The first "1" indicates the presence of the antigen "A" of the blood group "ABO" in attribute profile 195 of a red blood cell of a blood unit. The two (2) X's, "XX", in the seventh ($7^{th}$) and eighth ($8^{th}$) place of the attribute profile 195 indicate that it is not known whether or not the red blood cells have the antigens "K" and "k". The two zeros, "00", in the second ($2^{nd}$) and third ($3^{rd}$) position of the attribute profile 195 indicated that the red blood cell does not have the antigens "B" and "H". Since the attribute profile 195 includes X's or unknown entries the attribute profile 195 may be called a partial attribute profile 195. Some or all of the attribute profile 195 may need to be determined by the supplier 110 before selling the blood unit 150, or before the blood unit 150 is transfused into a recipient some or all of the antigen profile 195 of the red blood cell may need to be determined. As discussed above transfusion of a blood unit 150 with red blood cells with an antigen to a recipient whose red blood cells do not have the antigen may cause the recipient's immune system to react to the presence of the antigen. For example, if a blood unit 150 had red blood cells with an antigen profile that included antigen "B", and a recipient's red blood cells lacked the antigen "B", then a transfusion of red blood cells with the antigen "B" may cause the immune system of the recipient to react.

FIG. 2C illustrates an antigen profile 197 for a candidate blood unit 150 from the supplier 110 for a recipient with an antigen profile 195 of FIG. 2B. Antigen profile 197 "10010XX0110XX" is not compatible with antigen profile 195 "10010XX1010XX" because antigen profile 197 includes the antigen "Scii" which is indicated with a "1" in the ninth ($9^{th}$) place of the antigen profile 197. The antigen "Scii" may cause the immune system of the recipient with antigen profile 195 to react. FIG. 2D illustrates an antigen profile 199 "10010000010XX" that is compatible with antigen profile 195. The antigen profile 199 includes "$Do^a$", "E", and "A", but antigen profile 195 also includes antigens "$Do^a$", "E", and "A", so the recipient's immune system would not react to the antigens "$Do^a$", "E", and "A". Note that antigen profile 195 includes "Sci" and antigen profile 199 does not include "Sci". Often this will not cause a problem as the lack of an antigen on a red blood cell when the recipient's red blood cell does include the antigen does not cause the immune system to react. Therefore, antigen profile 199 is compatible with antigen profile 195 and may be used to satisfy the need 190. Note that other criteria may be used for being compatible. For example, it may not be possible or may be too expensive to insure that there are no antigens on the donor's red blood cells that are not on the recipient's red blood cells. A donor blood unit 150 may be deemed compatible despite the donor red blood cells including antigens that are not on the recipient's red blood cells. Additionally, a donor blood unit 150 may be deemed compatible despite the antigen profile of the donor's red blood cells not being fully known. As discussed above the need 190 may include an indication of how to determine whether or not a perishable item 150 meets a need 190.

Figure 3A:
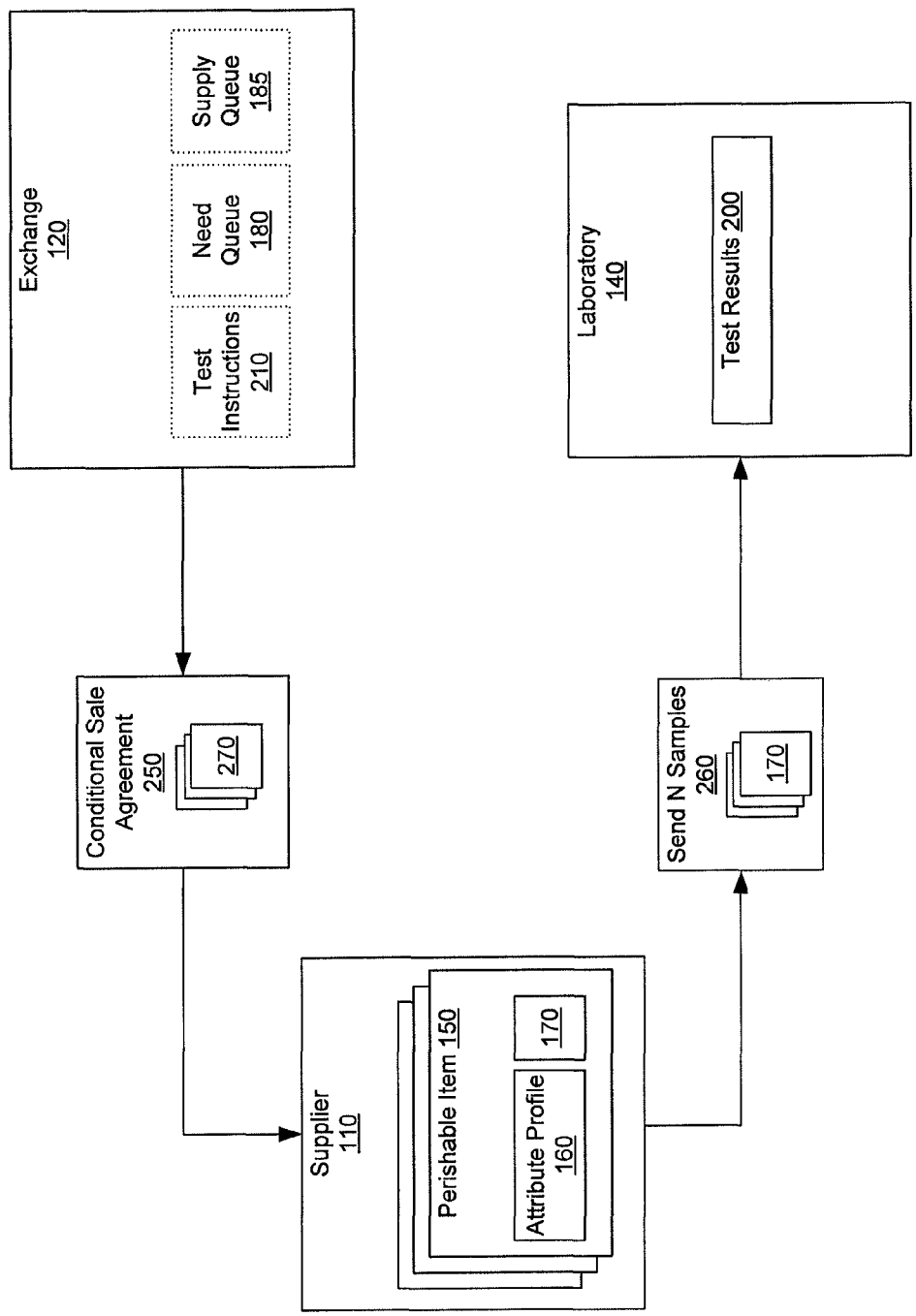
FIG. 3A is an illustration of an embodiment of a system for fulfilling requests for perishable items where a conditional sale agreement is used by the exchange to reserve the perishable items.

FIG. 3A is an illustration of an embodiment of a system for fulfilling requests for perishable items where a conditional sale agreement is used by the exchange to reserve the perishable items. In embodiments, the conditional sale agreement may be a call option. Illustrated in FIG. 3A are: the supplier 110, the exchange 120, and the laboratory 140. The exchange 120 enters with the supplier 110 into a conditional sale agreement 250. The supplier 110 reserves N perishable items 150 and sends 260 samples 170 for each of the reserved perishable items 150 to the laboratory 140. The supplier 110 may pool samples 170 and send the pooled samples 170 as well. The conditional sale agreement 250 includes compensation 270 (for example a fee) and is an arrangement (or agreement) in which the exchange 120 in return for the compensation 270 receives the right to inspect N perishable items 150 and the right to purchase the N perishable items 150 by a certain agreed-upon date of expiration which may be specified in the conditional sale agreement 250. In embodiments, the exchange 120 may receive the right to purchase L of the N perishable items 150 where L is less than N. In embodiments, the conditional sale agreement 250 may give the exchange 120 the right to purchase only perishable items 150 that are compatible with needs 190 that are presented in conjunction with entering into the conditional sale agreement 250. In embodiments, the conditional sale agreement 250 may give the exchange 120 the right to own perishable items 150 that are compatible with needs 190 that may be sent with the conditional sale agreement 250. The supplier 110 receives the conditional sale agreement 250 and compensation 270 and in return sends 260 N samples to the laboratory 140 and gives the exchange 120 the right to purchase the N perishable items 150 by a certain date. The exchange 120 may send test instructions 210 to the laboratory 210 and receive the test results 200, and interpret the test results 200 to determine which if any of the N perishable items 150 satisfies the need or needs in the need queue 180. In embodiments, the exchange 120 may be attempting to satisfy a single need 190 for a perishable item 150. In embodiments, the exchange 120 may be attempting to fulfill two or more needs 190 for perishable items 150. In embodiments, the exchange 120 may be attempting to fulfill a need 190 for the supply queue 185. In embodiments, the exchange 120 may be attempting to fulfill needs 190 expected to be made. In embodiments, the compensation 270 may be monetary. In embodiments, the compensation 270 may be other consideration such as obligating the exchange 120 to purchase (or arrange to have the perishable item requester 130 purchase) a certain number of perishable items 150.

Figure 3B:
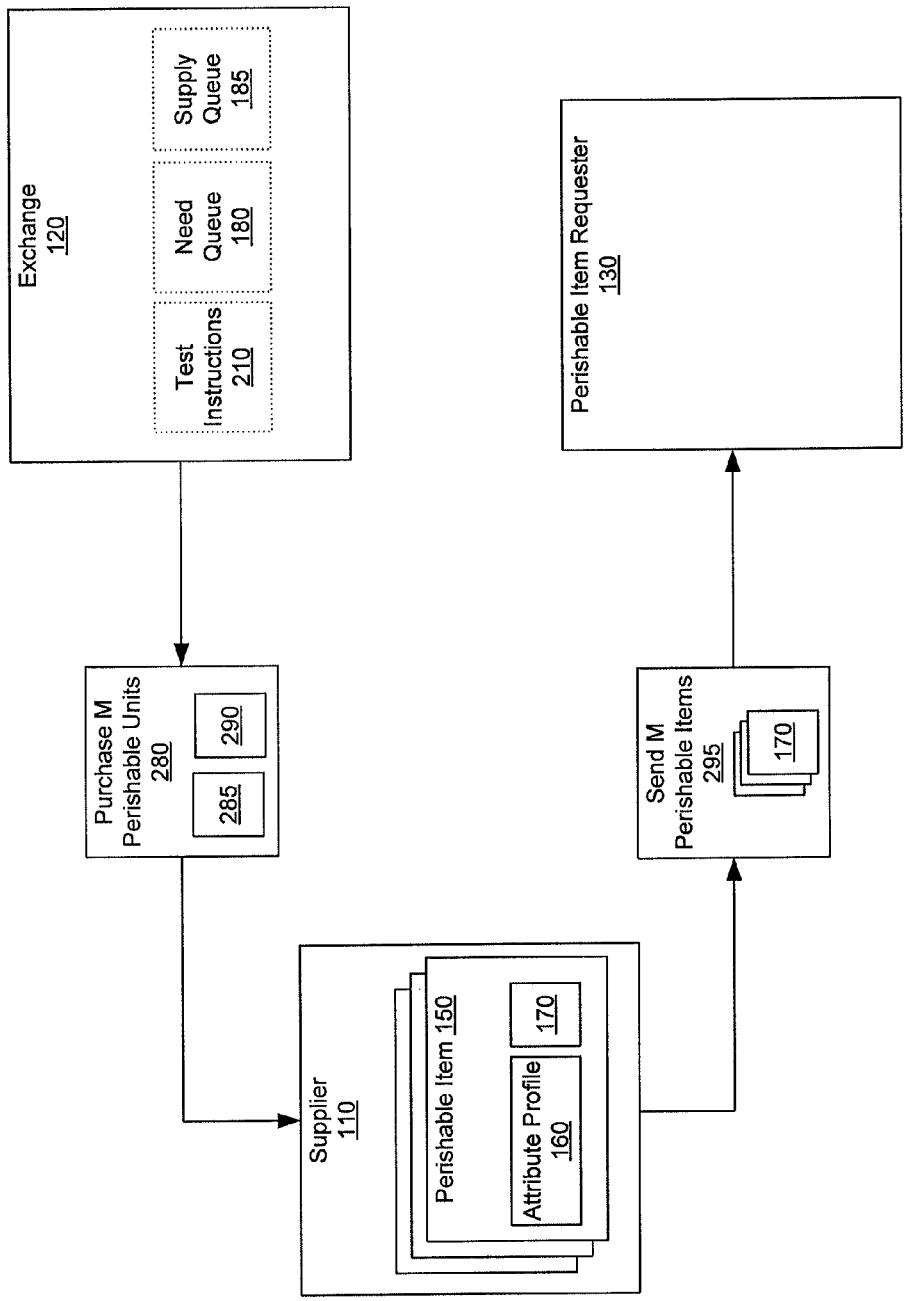
FIG. 3B is an illustration of an embodiment of a system for fulfilling requests for perishable items where a conditional sale agreement is used by the exchange to unreserve the perishable items and the need for perishable items is fulfilled.

FIG. 3B is an illustration of an embodiment of a system for fulfilling requests for perishable items where a conditional sale agreement is used by the exchange to unreserve the perishable items and the need for perishable items is fulfilled. Illustrated in FIG. 3B are the supplier 110, the exchange 120, and the perishable item requester 130. The exchange 120 exercises the conditional sale agreement 250 and purchases M of the N reserved perishable units 280 for compensation 290 and does not purchase the remaining N-M perishable units. The exchange 120 may send instructions 285 which indicate to the supplier 110 which perishable units 150 to send to the perishable item requester 130. The supplier 110 in return for the compensation 290 and according to the conditional sale agreement 250 sells M perishable units to the exchange 120 in for at least the compensation 290, and according to the instructions 285 sends M perishable items to the perishable item requester 130. In embodiments, the supplier 110 may send the perishable items 150 to multiple perishable item requesters 130. In embodiments, the exchange 120 may also indicate that the exchange 120 will not purchase the remaining N-M perishable items 150 prior to the expiration date of the conditional sale agreement 250. In embodiments, the perishable item requester 130 may send the compensation 290 to the supplier 110. In embodiments, the perishable item requester 130 may send instructions 285 to the supplier 110 indicating which of the perishable units 150 to send to the perishable item requester 130. In embodiments, the exchange 120 may purchase M perishable Units 280 for the supply queue 185. In embodiments, the exchange 120 may continue to reserve the M perishable units and unreserve the N-M perishable units 150.

The supplier 110 inventory will be reduced by M perishable units 150. In embodiments, the exchange 120 may replace the M perishable items sent to the perishable item requester 130. The exchange 120 may be obligated to replace the M perishable items sent to the perishable item requester 130 as part of the entering into the conditional sale agreement 250 with supplier 110 for reserving N perishable items. In embodiments, the exchange 120 may have to replace the M perishable items sent to the perishable item requester 130 with equivalent perishable items 150 in terms of age and mandatory or other tests performed by the supplier 110 on the perishable items 150.

In embodiments, the value of the compensation 270 of the conditional sale agreement 250 may be based on the probability of finding a perishable item 150 that is compatible with a need or multiple needs for perishable items 150.

In embodiments, the value of the compensation 270 of the conditional sale agreement 250 may not be based on the probability of finding a perishable item 150 that is compatible with a request or multiple requests for perishable items 150. The supplier 110 may charge the exchange 120 a base price (which may be a regular price charged customers) minus the compensation 290 for perishable items 150 the exchange 120 determines to use to fulfill requests. And, the supplier 110 may charge the exchange 120 a "shipping and handling" fee to cover the costs for shipping samples 170 to the laboratory 140 and/or shipping the perishable items 150 to the perishable item requester 130.

In embodiments, the exchange 120 may insure against the event of finding compatible perishable items 150 of the supplier 110. An insurance carrier would charge a premium based on the probability of the exchange 120 finding a perishable item 150 compatible with the attribute profile 195 of the request 190. The insurance carrier would pay for replacing perishable items 150 that were found to be compatible with the attribute profile 195 of the need 190 and shipped to the perishable item requester 130.

Figure 4:
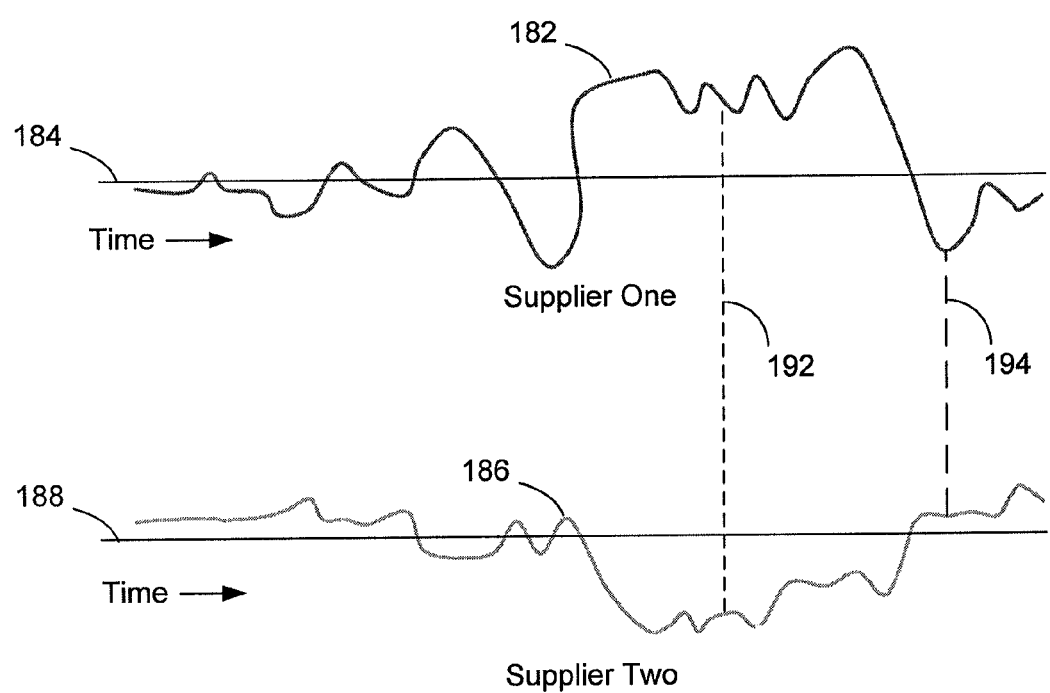
FIG. 4 illustrates an example of variations in the number of available units of perishable items for two suppliers.

FIG. 4 illustrates an example of variations in the number of available units of perishable items for two suppliers. Anticipated demand lines 184, 188 represent a number of units of perishable items needed to meet demand with time increasing from left to right. Actual supply curves 182, 186 represent actual supply of perishable items. When actual supply curves 182, 186 are above anticipated demand then there is sufficient supply to meet the anticipated demand 184, 188. When actual supply curves 182, 186 are below anticipated demand lines 182, 186 respectively, then there is not sufficient supply to meet anticipated demand lines 184, 188. When the actual supply curves 182 and 186 meet anticipated demand lines 184 and 188 respectively, then the supply of the perishable items exactly meets the demand. When the actual supply curves 182 and 186 are above the anticipated demand lines 184 and 188 respectively, then there is a surplus of perishable items. At a point in time at dotted line 192, supplier 1 has a surplus of perishable items and supplier 2 has a deficit of perishable items. At a point in time at dotted line 194, supplier 1 has a deficit of perishable items and supplier 2 has a surplus of perishable items. At dotted line 192, supplier 1 could provide surplus perishable items to supplier 2, but it may be difficult as supplier 1 and supplier 2 may not communicate with one another or supplier 1 and supplier 2 may communicate but infrequently. There may be many suppliers that provide supply locally or regionally. Both supplier 1 and supplier 2 may not have a reliable or predictable source of perishable items. For example, in the case of blood units, blood donors may be less likely to donate on a day with poor weather. Additionally, demand may be variable, and difficult to project and may be affected by unpredictable events. For example, a large accident may create a demand for many blood units. The exchange 120 (see FIG. 1) may have problems making an arrangement with a supplier 110 (see FIG. 1) to inspect and purchase perishable items because the supply and demand of perishable items may be unpredictable, which may make supplier 110 less likely to enter into an agreement with the exchange 120. Additionally, as discussed above, the price that supplier 1 and supplier 2 charge for a perishable item 150 may be different.

Figure 5A:
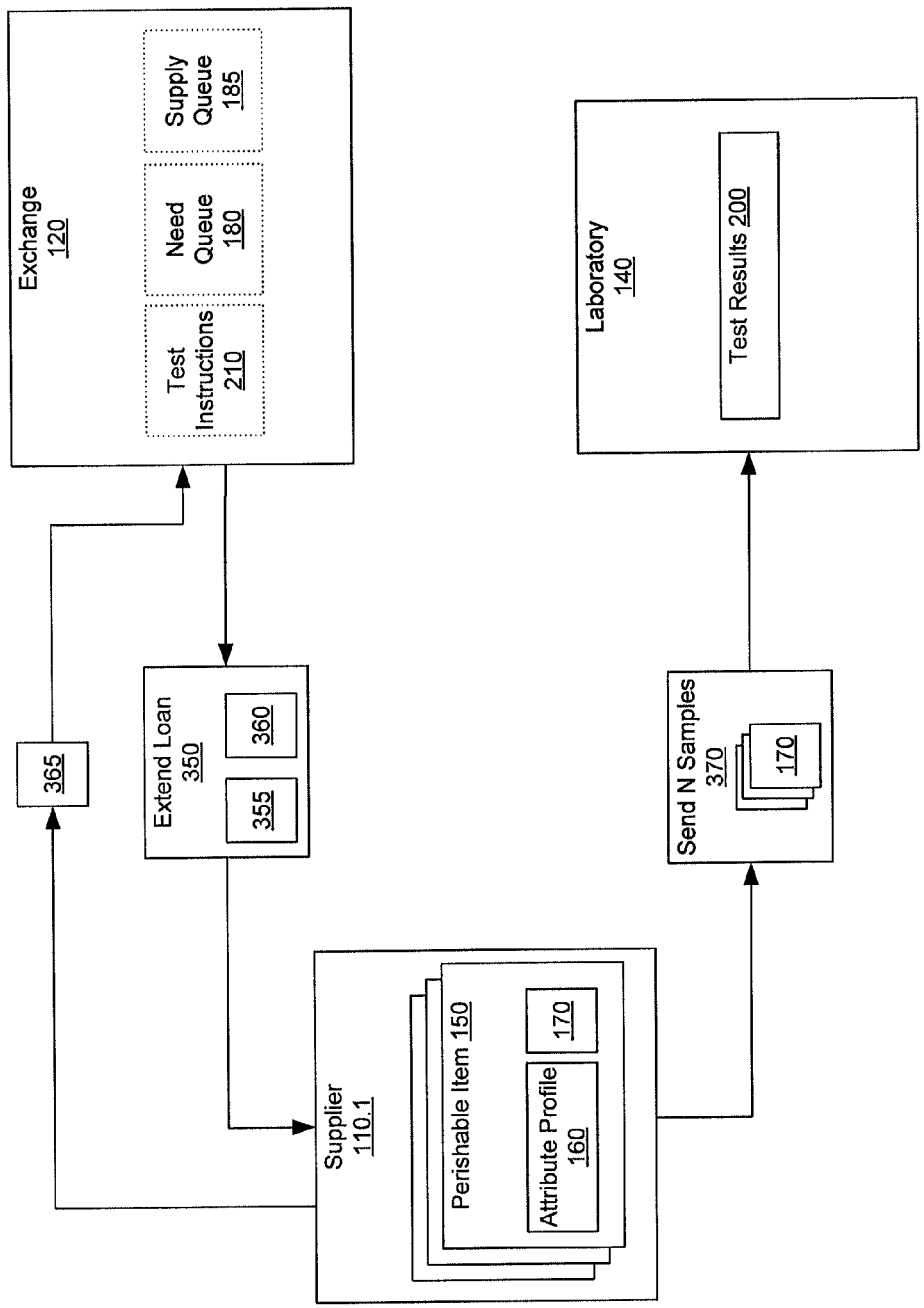
FIG. 5A is an illustration of an embodiment of a system for fulfilling needs for perishable items where repossession contracts are used by the exchange to reserve the perishable items.

FIG. 5A is an illustration of an embodiment of a system for fulfilling needs for perishable items where repossession agreements are used by the exchange to reserve the perishable items. In embodiments, the repossession agreement may be a repurchasing agreement. Illustrated in FIG. 5A are the supplier 110.1, the exchange 120, and the laboratory 140. Supplier 110.1 is referred to as supplier 110.1 because there will be more than one supplier in FIG. 5B. The exchange 120, under a repossession agreement, extends a loan 350 in exchange for (temporary) title 365 to N perishable items 150. The loan may include an interest rate 360 payable by the supplier 110.1 to the exchange 120). In embodiments, other considerations such as shipping and handling may be addressed by way of loan 350. The supplier 110.1 may send N samples 370 from the N perishable items to the laboratory 140 for testing. The supplier 110.1 may pledge as collateral the N perishable items 150. The supplier 110.1 may benefit from this arrangement as the supplier 110.1 may need a loan 350 and the N perishable items 150 may not be suitable collateral for conventional lending institutions such as a bank. Additionally, the interest rate 360 may be set to a below market rate. The supplier 110.1 may receive a fee for shipping and handling for sending the N samples to the laboratory 140. The supplier 110.1 may combine samples of the perishable items 150 prior to sending to the laboratory 140.

Figure 5B:
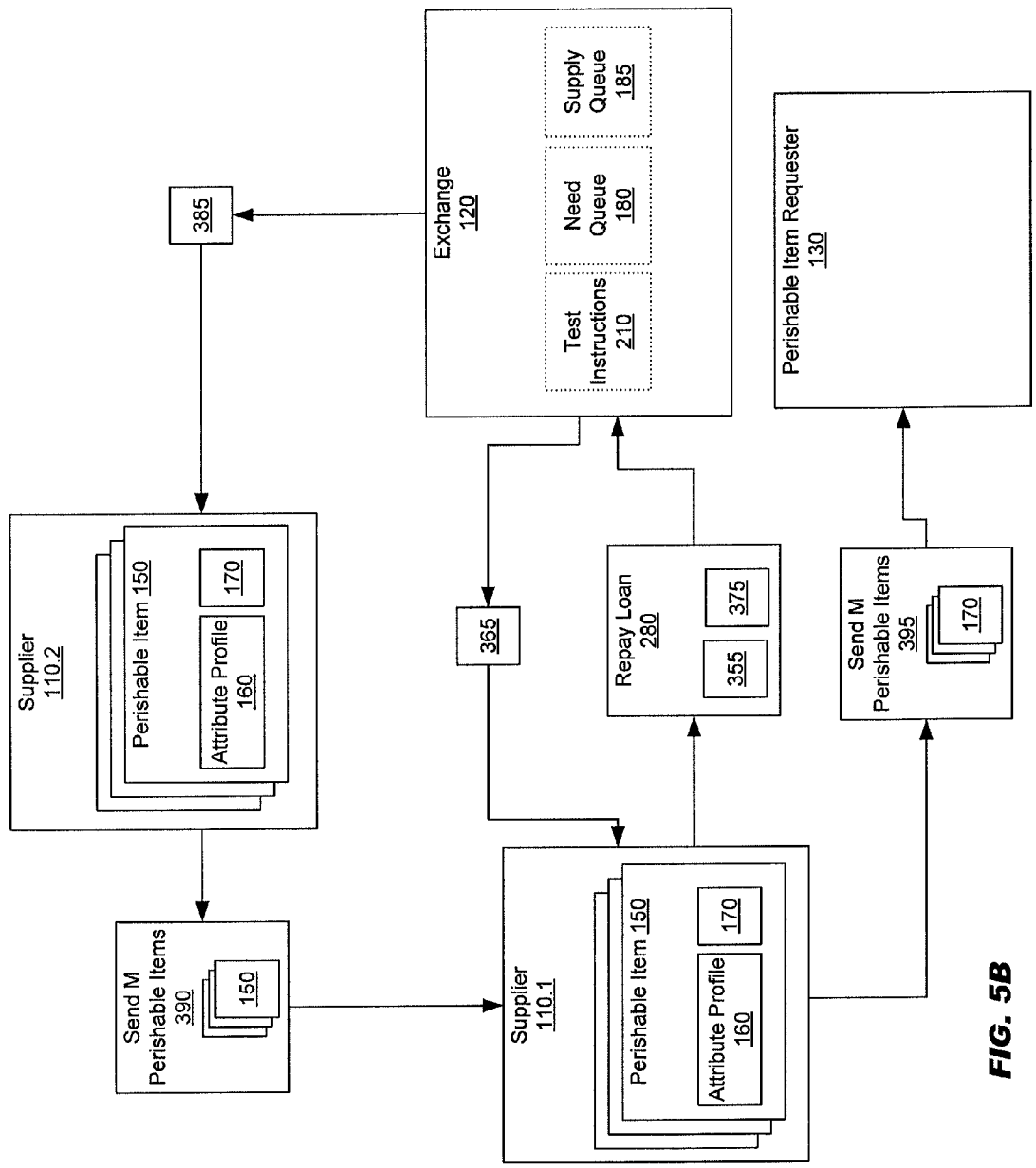
FIG. 5B is an illustration of an embodiment of a system for fulfilling requests for perishable items where a repossession agreement is used by the exchange to reserve the perishable items as described above.

FIG. 5B is an illustration of an embodiment of a system for fulfilling requests for perishable items where a repossession agreement is used by the exchange to reserve the perishable items as described above. Illustrated in FIG. 5B are the supplier 110.1, the supplier 110.2, the exchange 120, and the laboratory 140. The exchange 120 has determined which M of the N perishable items satisfy the need 190 and instructs the supplier 110.1 to send these M selected perishable items 395 to the perishable item requester 130 to fulfill the need received from the perishable item requester 130. The exchange 120 returns to the supplier 110.1 title 365 to the N-M perishable items 150 that are not selected and shipped to the perishable item requester 130. The supplier 110.1, in turn, repays the loan 355 and may pay interest 375. In embodiments, the exchange 120 may keep additional perishable items from the N-M perishable items 150 for the supply queue 185 or to satisfy other needs that may be on the need queue 180.

Optionally, the exchange 120 sends compensation 385 to the supplier 110.2 and in exchange the supplier 110.2 sends M perishable items 390 to the supplier 110.1. The M perishable items 150 that were sent to the perishable item requester 130 are then replaced with M perishable items 150 from the supplier 110.2. The perishable items 150 may be equivalent in terms of testing performed and time period remaining before expiration. In the alternative to sending compensation 385 to the supplier 110.2, the exchange 120 may purchase the M perishable items. In embodiments, the perishable item requester 130 purchases the M perishable items 395 from the supplier 110.1 or purchases the replacement perishable items 150 from the supplier 110.2. In embodiments, the m perishable items 395 may be keep in the supply queue 185 rather than being sent to the perishable item requester 130, and either be unreserved or sent to a perishable item requester 130 at a later time.

Figure 6:
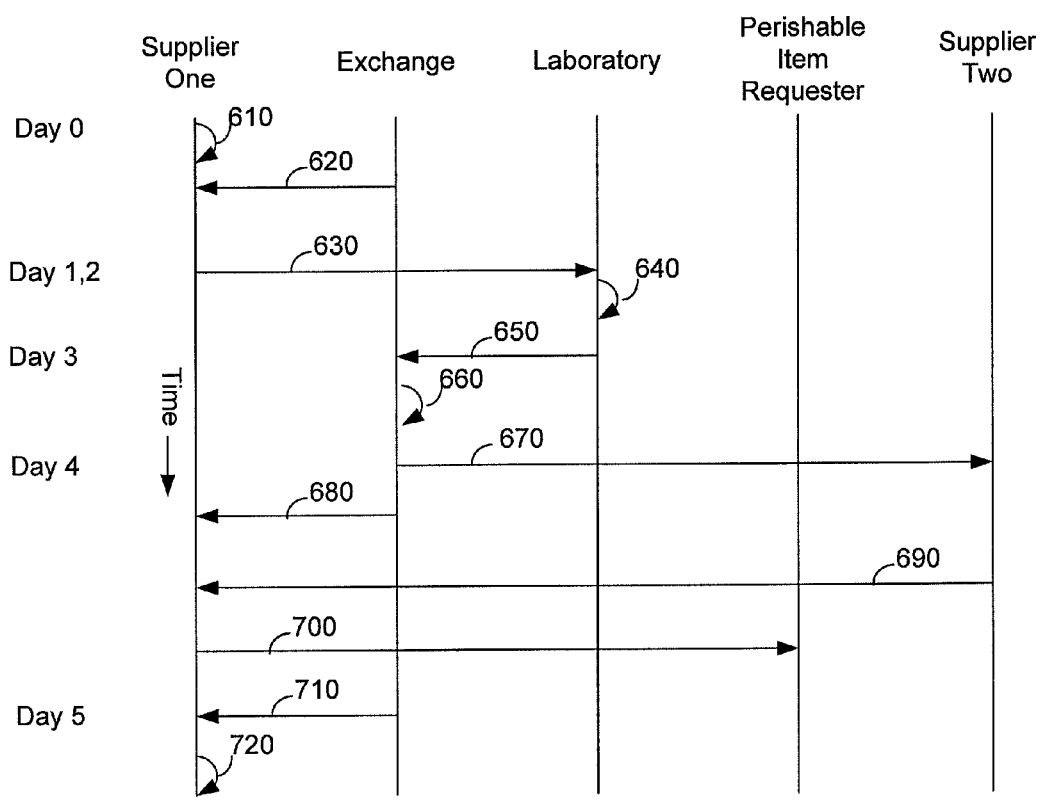
FIG. 6 illustrates the exchange reserving and unreserving perishable items, preferably during a mandatory pre-acceptance testing period incurred for newly collected or acquired perishable items by the supplier.

FIG. 6 illustrates the exchange reserving and unreserving perishable items, preferably during a mandatory pre-acceptance testing period incurred for newly collected or acquired perishable items by the supplier. Illustrated in FIG. 6 is time along the vertical axis and entities along the horizontal axis. The five (5) days along the vertical axis are meant to illustrate the time period incurred by the supplier for pre-acceptance testing of new perishable items before selling or distributing them. For example, for newly collected blood units, Supplier One may need to complete mandatory tests such as determining the blood type and screening for infectious agents such as Human Immunodeficiency Virus ("HIV") or Hepatitis C Virus ("HCV"). On Day 0, at 610, Supplier One receives new perishable items. At 620 the exchange may reserve the new perishable items under a repossession contract. On Day 1 and 2, at 630, Supplier One sends samples of the new perishable items to the laboratory. At 640, the laboratory performs tests and may determine the attribute profile of the new perishable items. On Day 3, at 650, the Laboratory sends the test results and/or the attribute profiles of the new perishable items to the Exchange. At 660, the Exchange determines which of the new perishable items satisfy a need for perishable items received by the Exchange. On Day 4, at 670 the Exchange purchases replacement perishable items for the perishable items the Exchange plans to ship, or cause to be shipped to the Perishable Item Requester. The purchased perishable items may be equivalent in terms of mandatory testing completed, and age, to the perishable items the Exchange will instruct Supplier One to ship to the perishable item requester. At 680, the Exchange instructs Supplier One as to which of the new perishable units are to be shipped to the Perishable Item Requester. At 690, Supplier Two ships the replacement perishable items to Supplier One to replace the perishable items that Supplier One will ship to the Perishable Item Requester. At 700, Supplier One, as per instructions from the Exchange, ships the specified perishable items to the Perishable Item Requester. On Day 5, at 710, the Exchange unreserves the perishable items that were reserved at 620 and not shipped at 700. At 720, Supplier One has completed the mandatory pre-acceptance testing of the perishable items, and Supplier One may now distribute the new perishable items including the perishable items that were the new perishable items at 610 and not shipped at 700, and, in this example, the replacement perishable items received at 690. The method described above has the advantage that Supplier One at the end of the mandatory pre-acceptance testing period has the same number of perishable items available to sell or distribute as new perishable items received at 610 despite fulfilling the needs of the Perishable Item Requester. The method described also has the advantage that the testing at 640 for finding perishable items compatible with the requests posted by the requester of perishable items was performed concurrently with the mandatory pre-acceptance testing for the new perishable items so that distribution of these perishable items was not delayed beyond the pre-acceptance testing period.

Figure 7:
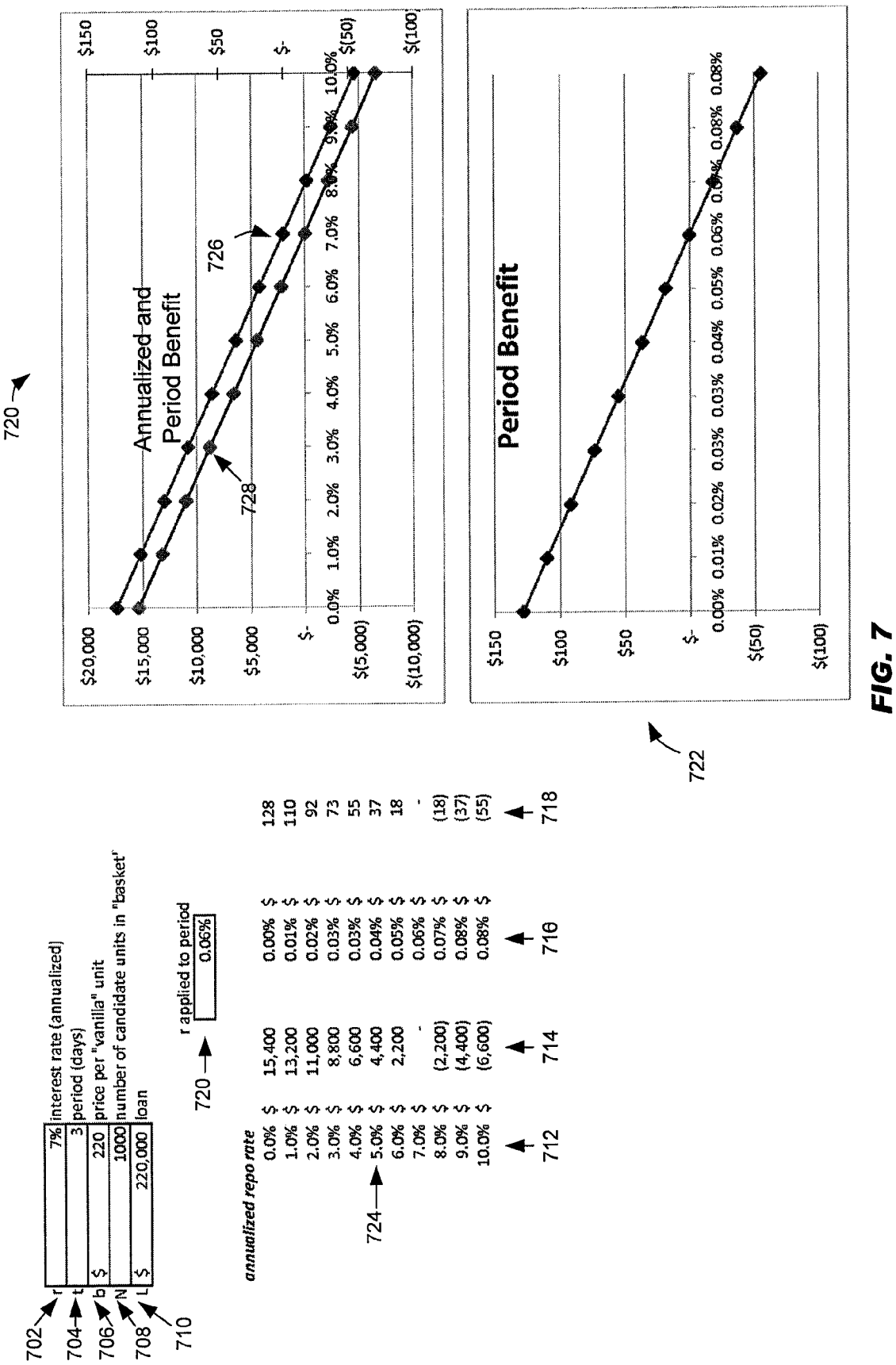
FIG. 7 illustrates the benefit to the supplier of a repossession loan.

FIG. 7 illustrates the benefit to the supplier of receiving a loan at a "below-market" interest rate under a repurchasing agreement. When the exchange uses a repossession loan to reserve and unreserve the perishable items, the exchange needs to determine a fair price for the loan. In the example of FIG. 7, it is assumed that the supplier could secure a commercial loan at an annualized interest rate 702 of seven percent (7%) from a lending institution. The supplier is assumed to want to borrow money and the repossession loan offers a means for the supplier to borrow money at less than the market rate in exchange for temporarily transferring title to reserved perishable units. The period 704 for the agreement is assumed to be three (3) days. The price 706 of a perishable item or blood unit (of a standard or "vanilla" type Supplier One would sell), as used in this example, is assumed to be $220 dollars, where a "vanilla blood unit" may mean a blood unit that has not undergone extensive antigen profile determination. The number of blood units 708 that are being reserved is one-thousand (1,000). The value of the loan 710 then is 1,000*$220 or $220,000. The interest rate applied 720 to a three-day period the time period that the exchange reserves the perishable items, in this example, is 0.06%. Column 712 shows different annual percentage rates that may be charged for the loan under the repossession loan agreement. Column 714 is the annualized benefit to the supplier resulting from the difference between the commercial rate of interest, 702, and these possible rates of interest available to the Supplier under a repossession agreement. The annualized benefit to the supplier assumes that the loan is rolled over so that the supplier extends the loan (under a renewing repurchasing agreement) for a year and continually reserves the same number of new blood units. Column 716 shows different rates of interest for the three-day period assumed in the example of the repossession agreement corresponding to the annualized percent rates 712. Column 718 shows the benefit realized by the supplier over the assumed three-day period, of securing a loan under the repurchasing agreement, corresponding to interest rates 716. For example, if the annualized percentage rate under the repossession agreement were 5% then row 724 would apply. The annualized benefit to the supplier would be $4,400 and the benefit to the supplier for a three-day loan would be $37 dollars with a three-day interest of 0.04%.

Graph 720 illustrates the annualized benefit, 728, and three-day benefit, 726, realized by the Supplier by securing the loan under a repurchasing agreement, given interest rates (from 0% to 10%) shown along the horizontal axis; shown along the left vertical axis is the annualized benefit to the supplier over the 7% rate the supplier could get from a lending institution and along the right vertical axis is the three-day period benefit.

Graph 722 illustrates the three-day period benefit of securing the loan under a repurchasing agreement: shown along the horizontal axis is the percentage interest rate for the assumed three-day period (from 0% to 0.08%) and along the vertical axis is the benefit to supplier (from $0 to $150). Note that since the rate of the loan from a lending institution was assumed to be 7% percent that at 7% percent in both graphs 720 and 722 the benefit to the supplier is $0.

The exchange may set the repossession loan based on the benefit to the supplier being as low as the supplier will enter into the repossession loan.

Figure 8:
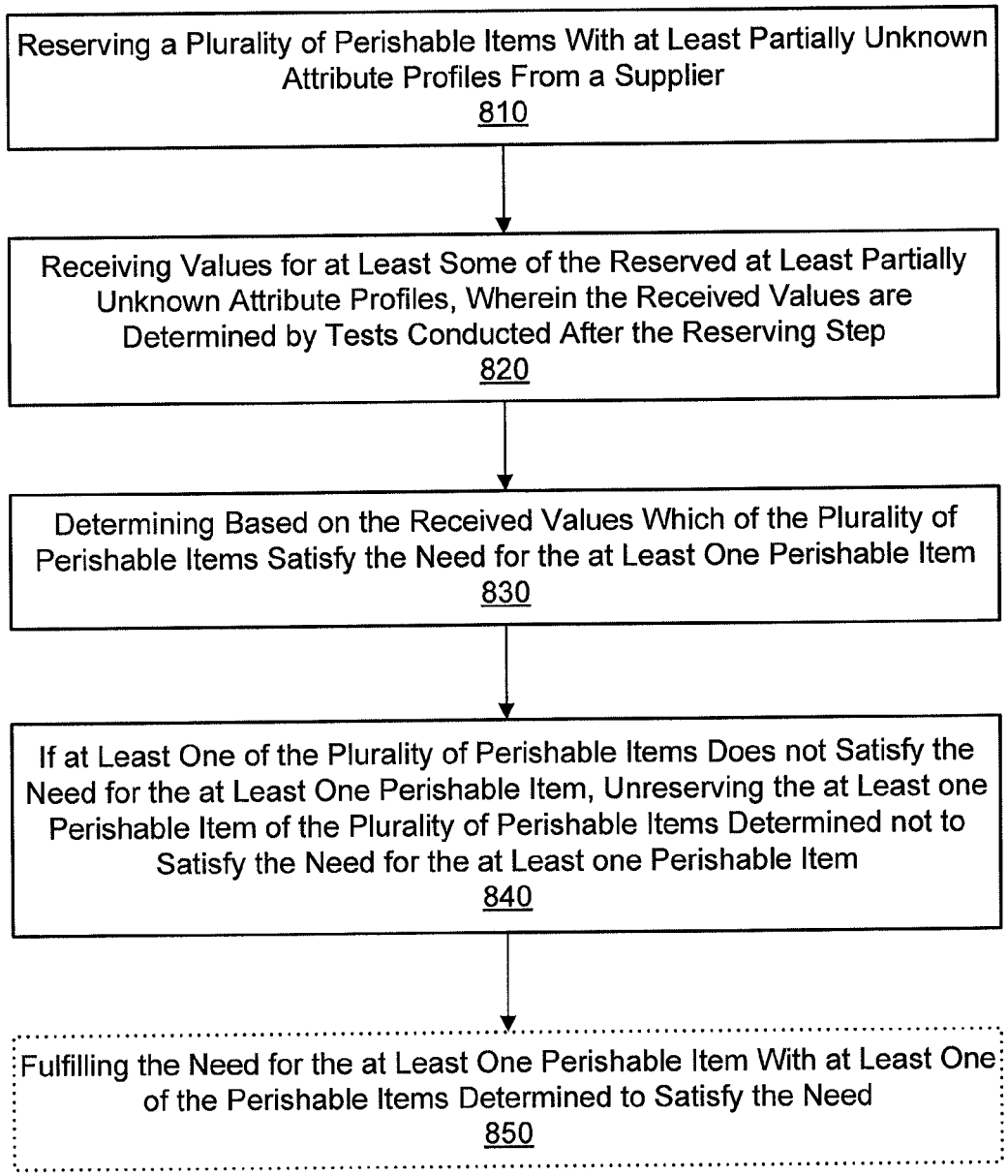
FIG. 8 illustrates a method of fulfilling a request for a perishable item.

FIG. 8 illustrates a method of fulfilling a need for at least one perishable item. The method begins at step 810 with reserving a plurality of perishable items with at least partially unknown attribute profiles from a supplier. The exchange 120 may calculate a number N of perishable items 150 to reserve in order to fulfill the need 190. The exchange 120 may then reserve N perishable items 150 from one or more suppliers 110. The exchange 120 may reserve the perishable items 150 with repossession contracts or conditional sale agreements, insurance, and/or a fee.

The method continues at step 820 with receiving values for at least some of the reserved at least partially unknown attribute profiles, wherein the received values are determined by tests conducted after the reserving. The exchange 120 may instruct the supplier 110 to send samples 170 of the N perishable items 150 to a laboratory 140 for testing, and the exchange 120, either directly or indirectly, sends test instructions 210 to the laboratory 140. The laboratory 140, either directly or indirectly, sends the test results 150 to the exchange 120.

The method continues at step 830 with determining based on the received values which of the plurality of perishable items satisfy the need for the at least one perishable item. The exchange 120 may use the test results 150 to determine which of the reserved perishable items 150 satisfies the need 190. The exchange 120 may determine if the need 190 is satisfied by determining if there is an attribute profile 160 of the reserved perishable items 150 that is compatible with the attribute profile 195 of the need 190.

The method continues at step 840 with if at least one of the plurality of perishable items does not satisfy the need for the at least one perishable item, unreserving the at least one perishable item of the plurality of perishable items determined not to satisfy the need for the at least one perishable item. The exchange 120 may unreserve the perishable items 150 that are not going to be used to fulfill the need 190. The exchange 120 may unreserve by electing not to exercise its conditional sale agreement to purchase reserved perishable items, or by closing a repossession contract and returning title to the supplier 120 for perishable items. The exchange 120 may reserve units by exercising its rights under such agreements and/or paying a fee.

Optionally, the method continues at step 850 with fulfilling the need for the at least one perishable item with at least one of the perishable items determined to satisfy the need. The exchange 120 may instruct the supplier 110 to ship a perishable item 150 determined to satisfy the need 190 to the perishable item requester 130. The method may then be completed.

Figure 9:
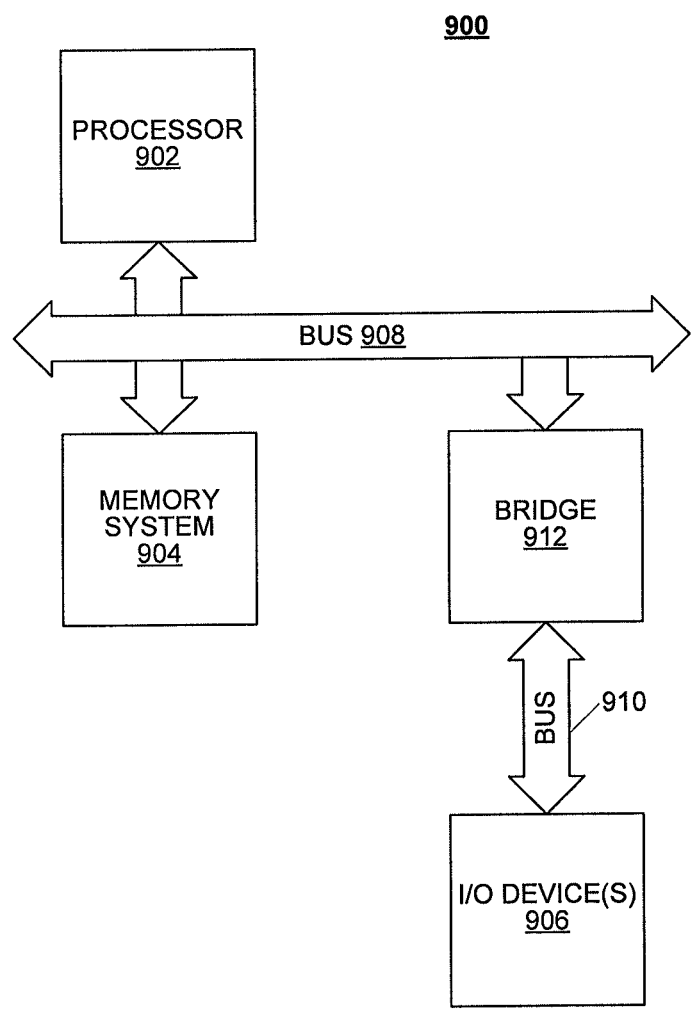
FIG. 9 is a simplified functional block diagram of a computer system.

FIG. 9 is a simplified functional block diagram of a computer system 900. The exchange can be implemented in hardware, software or some combination thereof. Additionally, some of the steps of embodiments of the method may be carried out by a human being. Additionally, some steps of receiving and/or sending data may be carried out by outputting data from the computer system 900 and inputting data into the computer system 900.

As shown in FIG. 9, the computer system 900 includes a processor 902, a memory system 904 and one or more input/output (I/O) devices 906 in communication by a communication "fabric." The communication fabric can be implemented in a variety of ways and may include one or more computer buses 908, 910 and/or bridge devices 912 as shown in FIG. 9. The I/O devices 906 can include network adapters and/or mass storage devices. Referring to FIGS. 1 and 9, the computer system 900 may receive requests 190 over the I/O devices 906 including networks for fulfilling a request for a perishable item and can send requests or instructions over the I/O devices 906 including networks to the supplier 110 to reserve perishable items 150 and for the supplier 110 to send samples 170 to the laboratory 140. Additionally, the exchange 120 may send test instructions 210 to the laboratory 140 and may receive the test results 150 over the I/O devices 906 including networks. The exchange 120, test instructions 210, test results 150, attribute profile 195, 160 and request queue 180 may reside on memory system 904 and/or on I/O devices 906. For example, the test instructions 210 may include a program to generate test instructions 210 which may include a database of information for assisting in generating the test instructions 210. The database may be part of the memory system 904, or may reside on a mass storage device that is accessible via the communication fabric and part of the I/O devices 906, which may be either local such as a hard disk in the same room as the processor 902 or may be located remotely such as in a memory system such as a hard disk remotely located in a service center. The communication fabric may be in communication with many networks including the Internet and local area networks. The exchange 120 may communicate with the laboratory either locally or remotely over the communication fabric to send test instructions 210 to the laboratory 140.

The modules described in connection with embodiments disclosed herein may be implemented where the number of modules is different with the functionality of described herein divided between fewer or more modules.

The various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Further, the steps and/or actions of a method or algorithm described in connection with the aspects disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from, and write information to, the storage medium. In the alternative, the storage medium may be integral to the processor. Further, in some aspects, the processor and the storage medium may reside in an ASIC. Additionally, the ASIC may reside in a user terminal. In the alternative, the processor and the storage medium may reside as discrete components in a user terminal. Additionally, in some aspects, the steps and/or actions of a method or algorithm may reside as one or any combination or set of instructions on a machine readable medium and/or computer readable medium, which may be in a physical form.

Although described in connection with preferred embodiments thereof, it will be appreciated by those skilled in the art that additions, deletions, modifications, and substitutions not specifically described may be made without departure from the spirit and scope of the invention as defined in the appended claims.

What is claimed is:

1. A method of operating a blood element inventory exchange system acting as an intermediary between a blood element supplier and a blood element requester to enhance a clinical value of, and to assign to the requester, at least one perishable blood element item, wherein the blood element is defined as a blood unit or cellular components of blood, the method comprising:

reserving, by the exchange, a set of perishable blood element items from the supplier predicted, according to a predetermined probability by the exchange, to contain items having an initially unknown desired blood element antigen attribute, wherein whether an item has the unknown desired blood element antigen attribute or not is unknown by both the exchange and the supplier and is not specified in a supplier's blood element product specification;

wherein:

the reserving comprises giving exclusive control to the exchange temporarily preventing a sale by the supplier of any of the reserved set of blood element items to the exchange by an agreement entered into between the exchange and the supplier;

the data records associated with the reserved set of blood element items are stored in a memory of a database of the inventory exchange system; and the perishable blood element items have a duration-dependent resource cost to the exchange for the reserving related to a respective usable life of each blood element;

the method further comprising:

determining, by a processor, which items of the reserved set of blood element items have the unknown desired blood element antigen attribute by performing a physical test on each item from the reserved set of blood element items by a tester designated by the exchange, to determine which blood element items of the reserved set of blood element items have the desired blood element antigen attribute, defined as desired items, wherein resource costs for performing each blood element antigen test is borne by the exchange, and the desired blood element item's clinical effectiveness is enhanced based on knowing the desired blood element antigen attribute of the desired blood element item;

receiving, by the exchange, results from the physical test performed on each blood element item identifying one or more blood element antigen types of the blood element;

storing, in a memory using a processor of the inventory exchange system, an indication as to which of the reserved set of blood element items are desired blood element items having the desired blood element antigen, thereby creating a virtual inventory of desired blood element items;

unreserving, by the exchange, blood element items determined not to have the desired blood element antigen attribute, wherein the unreserving comprises releasing the exclusive control given to the exchange of the blood element items;

receiving and aggregating requests from a plurality of blood element requesters for blood element items having a blood element antigen attribute profile that includes the initially unknown desired blood element antigen attribute, wherein the requests received by the exchange from a plurality of blood element requesters are stored in a request queue in a memory of the exchange and aggregating is performed by the processor; and matching the requests with blood element items in the virtual inventory based on the requested blood element antigen attribute profiles;

wherein the matching comprises determining compatibility between a requested blood element antigen profile and a blood element antigen profile in virtual inventory, according to a predefined antigen compatibility criterion.

2. The method of claim 1, further comprising, sequentially:

performing a further physical test on each item from the desired items by a tester designated by the exchange, to determine which items of the desired items have a second desired attribute, defined as finally desired items, wherein resource costs for performing each test is borne by the exchange, and wherein the testing is completed before the perishable item has perished;

storing, using a processor of the inventory exchange system, an indication as to which of the desired items are finally desired items in the memory;

unreserving, by the exchange, from the set of perishable blood element items, a first subset of items determined by the physical test to lack the desired attribute, defined as a first desired attribute, and unreserving, from a set of retained items, a subset determined to lack the second desired attribute, wherein the unreserving comprises releasing the exclusive control given to the exchange of the items.

3. The method of claim 1, further comprising:

determining a number of the set of perishable items based on at least: a) the resource cost for temporarily preventing the sale; b) a time intended for temporarily preventing the sale; and c) a resource cost for performing the physical test or measurement.

4. The method of claim 1, wherein the giving exclusive control to the exchange comprises:

receiving title to the set of perishable items from the supplier in exchange for a loan; and wherein the step of releasing the exclusive control given to the exchange comprises:

when at least one of the set of perishable items does not have the desired attribute, transferring the title to the at least one perishable item that does not have the desired attribute back to the supplier in exchange for repayment of the loan, and when at least one of the set of perishable items does have the desired attribute, replenishing the supplier with at least one equivalent perishable item for the at least one of the set of perishable items that does have the desired attribute.

5. The method of claim 4, wherein an interest rate charged for the loan is below a market rate.

6. The method of claim 4, wherein the set of perishable items with the unknown attribute is collateral for the loan.

7. The method of claim 1, wherein the step of giving exclusive control to the exchange comprises:

giving exclusive control to the exchange for a time that is less than a time that a particular item will perish.

8. The method of claim 1, wherein the step of giving exclusive control to the exchange comprises:
giving exclusive control to the exchange for a time that is greater than a time to perform the physical test or measurement.

9. The method of claim 1, wherein the step of giving exclusive control to the exchange comprises:
entering into a conditional sale agreement for the set of items; and
when the specific item does not have the desired item attribute, not exercising the conditional sale agreement for the specific item; and
when the specific item does have the desired item attribute, exercising the conditional sale agreement for the specific candidate item.

10. The method of claim 1, wherein the step of performing the physical test comprises:
instructing, by the exchange, the supplier to send a part of each of the reserved set of perishable items to a laboratory for testing; and
receiving antigen results of the testing as values for the unknown attribute.

11. The method of claim 10, further comprising:
instructing the laboratory how to perform the testing.

12. The method of claim 10, further comprising:
sharing the antigen results of the testing with the supplier in at least partial exchange for the duration dependent resource cost for the reserving.

13. The method of claim 10, wherein the part of each of the set of perishable items is a blood aliquot.

14. The method of claim 1, further comprising:
upon acceptance of a sale related to the requested item by the requester, initiating or coordinating, by the exchange, an order for the requested item by notifying the supplier possessing the requested item.

15. The method of claim 1, wherein the unknown desired attribute is not provided in initial communications between the exchange and the supplier prior to the reserving by the exchange.

16. The method of claim 1, wherein the matching comprises:
determining an incompatible match if a first category of an antigen is present in the attribute profile of the virtual inventory blood unit that is not present in the requested blood unit antigen profile; and
determining a compatible match if a second category of an antigen is present in the attribute profile of the virtual inventory blood unit that is not present in the requested blood unit antigen profile.

17. A method of fulfilling a need for a blood element wherein the blood element is defined as a blood unit or cellular components of blood, the method comprising:
entering, by a blood element exchange, into a conditional sale agreement for a set of perishable blood elements with at least partially unknown blood element antigen attribute profiles from a supplier, wherein:
the blood element antigen unknown attribute profiles have a blood element antigen attribute that is unknown by both the exchange and the supplier;
the unknown blood element antigen attribute is not specified in a supplier's product specification; and
the perishable blood elements have a duration-dependent resource cost to the exchange;
receiving values by a communications input of a processor of the exchange for at least some of the at least partially unknown blood element antigen attribute profiles based on performance of a physical antigen test on each of the blood elements to determine the unknown blood element antigen attribute by a tester designated by the exchange, wherein resource costs for performing each antigen test is borne by the exchange, and the tested blood element's clinical value and clinical effectiveness to be more accurately matched with a recipient is enhanced based on knowing the desired blood element antigen attribute of the desired blood element, and storing the values in a database residing in a memory of a computer associated with the exchange system;
determining, using the processor of the exchange system computer, based on the received values which of the set of blood elements satisfy the need for the blood element;
when at least one of the set of blood elements does not satisfy the need for the blood element, not exercising the conditional sale agreement for the at least one of the set of blood elements determined not to satisfy the need for the at least one blood element;
when at least one of the set of blood elements does satisfy the need for the blood element, exercising the conditional sale agreement for the at least one of the set of blood elements determined to satisfy the need for the at least one blood element; and
fulfilling the need for the blood element with the at least one of the set of blood elements determined to satisfy the need for the at least one blood element, wherein at least one step is executed by a processor of a computer;
wherein the determining of which of the set of blood elements satisfy the need for the blood element comprises:
determining an antigen compatibility between a requested blood element antigen profile and a virtual inventory blood element antigen profile according to a predefined antigen compatibility criterion.

18. The method of claim 17, wherein the step of receiving values for at least some of the at least partially unknown attribute profiles comprises:
instructing the supplier to send a part of each of the set of blood elements with at least partially unknown antigen profiles to a laboratory for testing;
representing the set of blood elements with at least partially unknown antigen profiles in a computer memory;
receiving values for at least some of the at least partially unknown antigen profile; and
updating the representation of the set of blood elements with at least partially unknown antigen profiles with the received values.

19. The method of claim 17, further comprising:
determining, by use of the processor, a number of the set of perishable items based on a probability of finding an antigen profile that will satisfy the need for the blood element.

20. A non-transitory computer program product, comprising a computer usable medium having a computer readable program code embodied therein, said computer readable program code when executed performs the steps of:
reserving, by the exchange, a set of perishable blood element items from the supplier predicted, according to a predetermined probability by the exchange, to contain items having an initially unknown desired blood element antigen attribute,
wherein whether an item has the unknown desired blood element antigen attribute or not is unknown by both the exchange and the supplier and is not specified in a supplier's blood element product specification;
wherein:
the reserving comprises giving exclusive control to the exchange temporarily preventing a sale by the supplier of any of the reserved set of blood element items to the exchange by an agreement entered into between the exchange and the supplier;

the data records associated with the reserved set of blood element items are stored in a memory of a database of the inventory exchange system; and the perishable blood element items have a duration-dependent resource cost to the exchange for the reserving related to a respective usable life of each blood element;

the steps further comprising:

determining, which items of the reserved set of blood element items have the unknown desired blood element antigen attribute by performing a physical test on each item from the reserved set of blood element items by a tester designated by the exchange, to determine which blood element items of the reserved set of blood element items have the desired blood element antigen attribute, defined as desired items, wherein resource costs for performing each blood element antigen test is borne by the exchange, and the desired blood element item's clinical effectiveness is enhanced based on knowing the desired blood element antigen attribute of the desired blood element item;

receiving, by the exchange, results from the physical test performed on each blood element item identifying one or more blood element antigen types of the blood element;

storing, in a memory using a processor of the inventory exchange system, an indication as to which of the reserved set of blood element items are desired blood element items having the desired blood element antigen, thereby creating a virtual inventory of desired blood element items;

unreserving, by the exchange, blood element items determined not to have the desired blood element antigen attribute, wherein the unreserving comprises releasing the exclusive control given to the exchange of the blood element items;

receiving and aggregating requests from a plurality of blood element requesters for blood element items having a blood element antigen attribute profile that includes the initially unknown desired blood element antigen attribute, wherein the requests received by the exchange from a plurality of blood element requesters are stored in a request queue in a memory of the exchange and aggregating is performed by the processor; and matching the requests with blood element items in the virtual inventory based on the requested blood element antigen attribute profiles;

wherein the matching comprises determining compatibility between a requested blood element antigen profile and a blood element antigen profile in virtual inventory, according to a predefined antigen compatibility criterion.

21. A computer system of a blood element inventory exchange system for fulfilling a need for at least one perishable blood element item, wherein the blood element is defined as a blood unit or cellular components of blood, the system comprising:

a memory that contains a database associated with the exchange system;

a processor comprising software modules adapted to:

reserve a set of perishable blood element items with at least partially unknown blood element antigen attribute profiles from a supplier, wherein:

the unknown blood element antigen attribute profiles have a blood element antigen attribute that is unknown by both the exchange and the supplier;

the unknown blood element antigen attribute is not specified in a supplier's product specification;

the perishable blood element items have a duration-dependent resource cost to the exchange; and the reserving comprises giving exclusive control to the exchange by the supplier of any of the reserved set of blood unit items to a third party by a communication between the exchange and the supplier over a networked interface;

the processor further adapted to:

receive values by a communications input of the processor for at least some of the at least partially unknown blood element antigen attribute profiles based on performance of a physical antigen test on each blood element to determine the unknown antigen attribute by a tester designated by the exchange, wherein resource costs for performing each antigen test is borne by the exchange, and the tested item's clinical value and clinical effectiveness is enhanced based on knowing the desired antigen attribute of the desired item, and storing the values in a database residing in a memory of a computer associated with the exchange system;

determine based on the received values which of the set of perishable blood element items satisfy the need for the at least one perishable blood element item; and unreserve at least one perishable blood element item of the set of perishable blood element items determined not to satisfy the need for the at least one perishable blood element item, if at least one of the set of perishable blood element items does not satisfy the need for the at least one perishable blood element item, wherein the unreserving comprises releasing the exclusive control given to the exchange of the blood element items.

* * * * *